(12) United States Patent
Wallenås

(10) Patent No.: US 8,282,828 B2
(45) Date of Patent: Oct. 9, 2012

(54) SYSTEM AND METHOD FOR REGENERATION OF A FLUID

(75) Inventor: Anders Wallenås, Lomma (SE)

(73) Assignee: Triomed AB, Lund (SE)

( * ) Notice: Subject to any disclaimer, the term of this patent is extended or adjusted under 35 U.S.C. 154(b) by 516 days.

(21) Appl. No.: 12/377,602

(22) PCT Filed: Aug. 16, 2007

(86) PCT No.: PCT/SE2007/000730
§ 371 (c)(1),
(2), (4) Date: Aug. 25, 2009

(87) PCT Pub. No.: WO2008/020801
PCT Pub. Date: Feb. 21, 2008

(65) Prior Publication Data
US 2010/0234795 A1    Sep. 16, 2010

(30) Foreign Application Priority Data
Aug. 16, 2006 (SE) ........................... 0601688

(51) Int. Cl.
*B01D 11/00* (2006.01)
*B01D 61/00* (2006.01)
*C02F 1/44* (2006.01)

(52) U.S. Cl. ............ 210/645; 210/195.2; 210/646; 210/652; 210/772; 210/791; 604/29

(58) Field of Classification Search .................. None
See application file for complete search history.

(56) References Cited

U.S. PATENT DOCUMENTS
3,926,797 A    12/1975 Gigou et al.
4,351,710 A *  9/1982 Jain ........................... 204/522

FOREIGN PATENT DOCUMENTS
WO    WO 2006/088419 A2    8/2006
* cited by examiner

*Primary Examiner* — Vickie Kim
*Assistant Examiner* — Dirk Bass
(74) *Attorney, Agent, or Firm* — Capitol City TechLaw

(57) ABSTRACT

A method and a system for regenerating a body fluid, such as a peritoneal dialysis fluid. The body fluid is removed into an extracorporeal circuit comprising an electrofilter for removing charged ions from the body fluid, a nanofilter for removing large molecules, such as Dextran 40, and a reverse osmosis filter for concentrating the body fluid, for producing a synthetic urine to be discarded. The removed ions and large molecules are returned to the patient together with pure water from the reverse osmosis filter through an ultrafilter.

8 Claims, 8 Drawing Sheets

SYSTEM AND METHOD FOR REGENERATION OF A FLUID

AREA OF INVENTION

The present invention relates to a method and a system for blood purification and for removal of soluble products from a body fluid. The system is particularly intended for removal of waste products from a patient having impaired or no kidney function.

BACKGROUND OF THE INVENTION

The international patent application No. PCT/SE2006/000212 filed Feb. 16 2006 with priority claimed from Feb. 16, 2005, discloses a system and method for regeneration of a fluid, in which synthetic urine is formed from a body fluid by only filtering and concentration. The synthetic urine will consequently include the substances and ions of the body fluid in the same proportions as in the body fluid but concentrated, except from larger molecules like albumin, which are filtered out before concentration. The body fluid may be plasma obtained from a plasma filter or peritoneal dialysis fluid obtained from the peritoneal cavity of a patient. Alternatively, the body fluid may be whole blood passed on one side of a semi-permeable membrane whereby the regenerated fluid is circulated on the other side of the membrane.

Because it is difficult to separate urea and creatinine from sodium and potassium, such substances are excreted in the synthetic urine in the same concentrations as found in the body fluid. While excretion of urea and creatinine is desired, excretion of sodium and potassium should be minimized. Small amounts of excretion can be replaced by oral intake.

The present invention starts from the fact that some patients produce creatinine at such a rate that the blood level of creatinine could reach poisonous levels if not excreted at high rates.

SUMMARY OF THE INVENTION

Accordingly, it is an object of the present invention to provide a system and method for regenerating a fluid and providing synthetic urine, in which a sufficient amount of creatinine is excreted to balance production in the body and in which the excretion of small ions, such as sodium and potassium, is maintained at an acceptable level.

According to a first aspect of the present invention there is provided a system for regeneration of a body fluid, comprising: a line for removing a body fluid from a patient; a filter unit for retaining at least one component of the body fluid as a retentate fluid and for passing other components as a permeate fluid; a concentrating unit for concentrating the permeate fluid of the filter means, for producing a synthetic urine to be discarded as a retentate fluid and essentially water as a permeate fluid; a line for returning the permeate fluid of the concentrating unit and the retentate fluid of the filter means to the body of the patient; and an electrofilter for removing charged ions from the body fluid and returning said ions to the patient.

The concentrating unit may be a reverse osmosis filter. The electrofilter may be arranged before said reverse osmosis filter. Alternatively, or additionally, an electrofilter may be arranged after said reverse osmosis filter for removing charged ions from the synthetic urine.

In an embodiment, the electrofilter comprises an anode and a cathode and ion exchange membranes, whereby a source of electric power is to be applied over the anode and cathode. A first compartment may be formed in the electrofilter between a cation membrane and an anion membrane, in which said body fluid may be entered, and a second compartment may be formed at the other side of the cation membrane and a third compartment may be formed at the other side of the anion membrane, wherein a flushing fluid may be arranged to pass through said second and third compartment in order to flush out the ions separated by the membranes. The flushing fluid may be the retentate fluid of the filter means or the permeate fluid of the reverse osmosis means.

In another embodiment, the system further comprises an ultrafilter arranged in the return line to the patient.

The filter unit may be a nanofilter having a membrane with a cut-off of about 500 Da.

In another aspect, there is provided a method for regenerating a body fluid, comprising: removing a body fluid from a patient; removing charged ions from the body fluid and returning said ions to the patient; filtering said body fluid in a filter unit for retaining at least one component of the body fluid as a retentate fluid and for passing other components as a permeate fluid; concentrating said permeate fluid of the filter means, for producing a synthetic urine to be discarded as a retentate fluid and essentially water as a permeate fluid; and returning the permeate fluid of the concentrating unit and the retentate fluid of the filter means to the patient.

BRIEF DESCRIPTION OF DRAWINGS

Other objects, features and advantages of the invention will become apparent from the following detailed description of several embodiments of the invention with reference to the drawings, in which.

DETAILED DESCRIPTION OF EMBODIMENTS

The embodiments described below are given for a skilled person to be able to carry out the invention. The different features of the embodiments can be combined in other manners than described below. The invention is not limited to the described embodiments.

Figure 1:
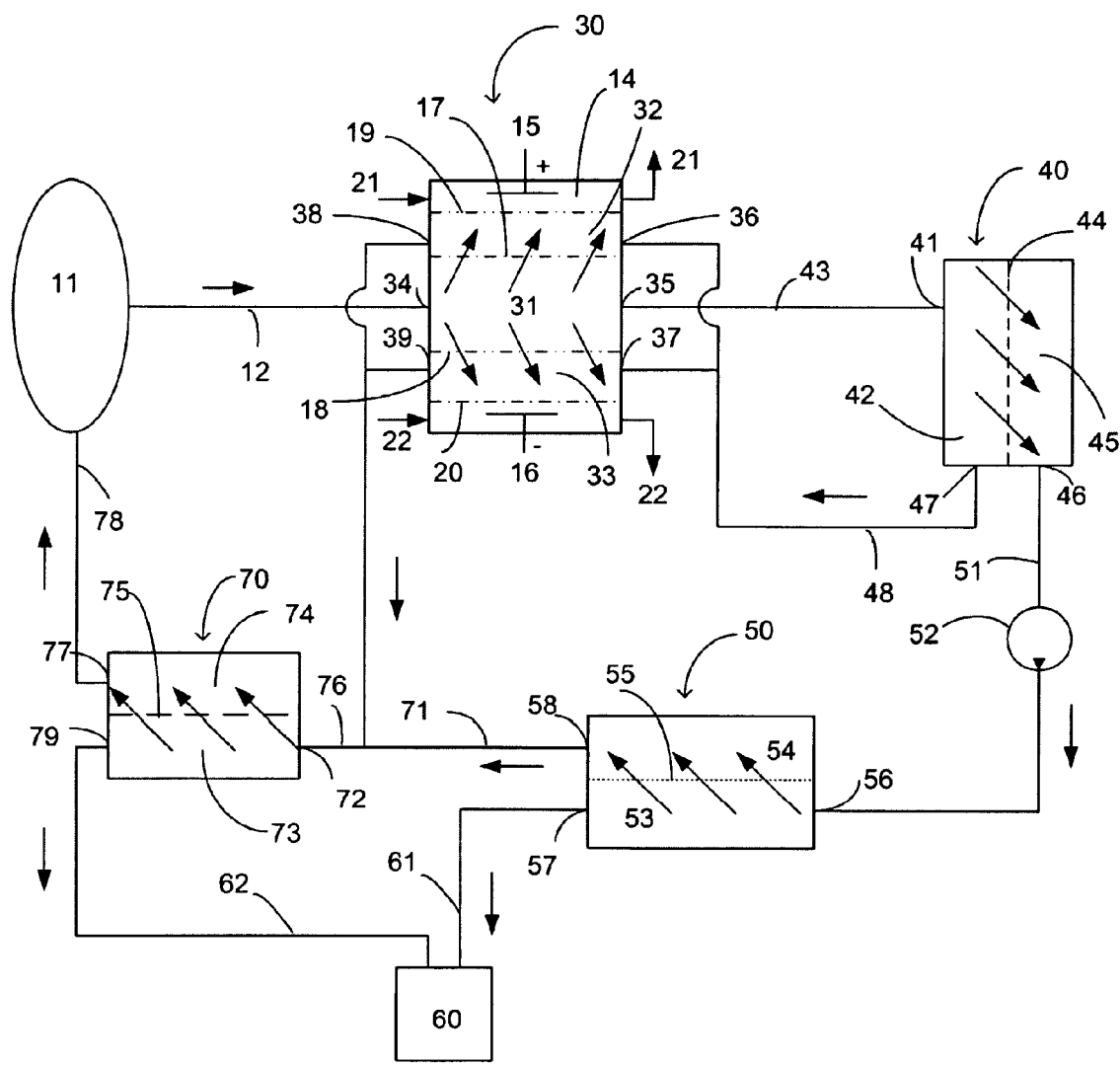
FIG. 1 is a schematic view of an embodiment of the invention.

FIG. 1 is a schematic view of a first embodiment of the invention. Reference numeral 11 schematically illustrates a source of a body fluid.

The body fluid is a fluid obtained from the body of a patient, generally a mammal. Such body fluid may be peritoneal dialysis fluid installed in the peritoneal cavity of patient and accessible via one or several catheters. Alternatively, the body fluid may be a fluid obtained from a filter comprising a semi-permeable membrane, one side of which blood is flowing and the other side of which the body fluid is present, as in conventional dialysis. The body fluid may be plasma obtained by filtering the blood. The body fluid may be a fluid, which is equilibrated with the blood via a semi-permeable membrane via diffusion of ions and substances across the membrane, or a combination of diffusion and convection. Other body fluids may as well be provided.

Thus, in the case of a peritoneal dialysis fluid as a body fluid, the fluid comprises among others the following groups of ions and substances:
1) sodium, potassium, calcium, magnesium
2) urea, creatinine,
3) beta-2-microglobuline
4) Dextran 40, albumin,
5) bacteria, virus, debris Dextran 40 is a polysaccharide used as an osmosis agent for provoking water transport over the peritoneal membrane to the peritoneal fluid for water removal from the patient. Other osmotic agents may be used as well, such as glucose, Icodextrin®, etc The body fluid in the receptacle 11 is transported by means of a line 12 to an inlet 34 of a first compartment 31 of a first filter, which in the embodiment shown in FIG. 1 is an electrofilter 30.

The electrofilter 30 comprises an anode 15 and a cathode 16 marked with plus and minus, respectively, in FIG. 1. The fluid entering a compartment 31 of the electro-filter passes along two membranes, a cation exchange membrane 17 arranged at the anode side and an anion exchange membrane 18 arranged at the cathode side. The cation exchange membrane is negatively charged and passes negatively charged ions, such as chloride ions. The anion exchange membrane is negatively charged and passes positively charged ions, such as sodium and potassium. Before the chloride ions passing the cation membrane 17 reach the anode 15, another anion ion exchange membrane 19 is arranged, through which the negatively charged ions cannot pass. In the same way, another cation ion exchange membrane 20 is arranged surrounding the cathode so that the positively charged ions cannot reach the cathode. Between membranes 17 and 19, there is formed a second compartment 32 for negatively charged ions. Between membranes 18 and 20, there is formed a third compartment 33 for positively charged ions.

Adjacent the anode 15, there is produced oxygen gas $O_2$ and around the cathode 16 there is produced hydrogen gas $H_2$. These gases are removed by a rinse solution as indicated by arrows 21 and 22, respectively.

Thus, the electrofilter 30 is effective in removing charged ions from the body fluid entering the first compartment 31 of the electro-filter, such as the ions indicated under group 1) above. The electrofilter is most effective in removing one valence ions, such as sodium and potassium ions, and less effective in removing two valence ions, such as calcium and magnesium.

The fluid of compartment 31, i.e. the retentate fluid, exits the electro-filter 14 via a retentate outlet 35 and via a line 43 leading to an inlet 41 of a first compartment 42 of a second filter 40.

The second filter is a so called nanofilter and comprises a semipermeable membrane 44 having a pore size in the nanometer area, such as about 1 nm corresponding to a size exclusion of 200 Da. The second filter comprises a second compartment 45 comprising a permeate outlet 46 for matter passing the membrane, the permeate fluid. Moreover, the second filter comprises a retentate outlet 47 for the retentate fluid not passing the membrane.

The permeate fluid of the second filter passing the membrane comprises ions which may pass the filter, such as small substances as indicated in group 2) above, i.e. urea and creatinine, and any sodium and potassium left. The substances of groups 3), 4) and 5) are so large that they do not pass the membrane 44 of the nanofilter.

The permeate fluid exits the nanofilter via permeate outlet 46 and passes via a line 51 to an inlet 56 of a concentration device 50. The concentration device 50 may be a third filter, such as a reverse osmosis (RO) unit, having a first compartment 53 and a second compartment 54 separated by a reverse osmosis membrane 55 having very small pores and essentially only passing water ($H_2O$). Since a large osmotic pressure prevails over the osmotic membrane, a pump 52 is arranged in the line 51 in order to increase the pressure in the first compartment 53.

The fluid in the first compartment 53 of the RO filter, i.e. the permeate fluid from nanofilter 40 comprises only few substances passing the nanofilter membrane. Moreover, the permeate fluid from nanofilter 40 lacks the ions separated by the electro-filter, which means that the osmotic pressure over the reverse osmosis membrane will not be excessively high. The osmotic pressure is negatively proportional to the size of the substances. Since the smallest substances, such as sodium and potassium, are removed in the electrofilter 30, the pressure required to be produced by pump 52 may be small, such as around 10 Bar. The pressure and flow rate are controlled so that a desired concentration of the retentate fluid present in the first compartment 53 is obtained. In one embodiment, the concentration ratio should be about 15:1.

The retentate fluid of the RO filter 50 present in compartment 53 comprises urea and creatinine concentrated in the desired ratio, such as 15:1. This retentate fluid exits the RO filter via a retentate outlet 57 and a line 61 to a vessel 60 for collecting synthetic urine.

The permeate fluid of the RO filter, i.e. pure water, is lead from the second compartment 54 via permeate outlet 58 and line 71 to an inlet 72 of an ultrafilter 70. The ultrafilter comprises a first compartment 73 and a second compartment 74 separated by a membrane 75 having a pore size excluding substances larger than about 50000 Da. The operation of the ultrafilter will be explained in more detail below.

The retentate fluid of the nanofilter 40 still present in the first compartment 42 exits the nanofilter via retentate outlet 47 and a line 48 to an inlet 36 to the second compartment 32 and to an inlet 37 to the third compartment 33 of the electrofilter 30. The fluids in compartments 32 and 33 exit the electrofilter via outlets 38 and 39 and a common line 76 to the inlet 72 of the ultrafilter, where it combines with the water from the RO filter 50 in line 71. Thus, the ions passing the anion and cation membranes 17 and 18, i.e. group 1) sodium, potassium and chloride ions, are passed to the ultrafilter 70. Moreover, the substances that are retained by the nano-filter membrane, i.e. group 3) beta-2-microglobuline, group 4) Dextran 40, albumin and group 5), bacteria, virus and debris, are passed to the ultrafilter. The permeate fluid of the ultrafilter in compartment 74 exits the ultrafilter via permeate outlet 77 and line 78 to the body fluid compartment 11, such as the peritoneal cavity. The retentate fluid of the ultrafilter 70 in compartment 73 exits the ultrafilter via retentate outlet 79 and line 62 to the vessel 60. The retentate fluid includes all substances that cannot pass through the membrane, which is essentially group 5) bacteria, virus and debris, and albumin from group 4). Dextran 40 can easily pass the membrane of the ultrafilter. However and unexpectedly, beta-2-microglobuline does not pass the ultrafilter to any appreciable extent, but is removed together with the retentate.

The ultrafilter may be replaced by a sterile filter of conventional design, for example having a cut-off of about 200000 Da. In this case, albumin and beta-2-microglobuline will pass the filter and will not be excreted.

The system according to the embodiment shown in FIG. 1 is controlled by several pumps, valves and/or restrictions in order to obtain the desired operation. The following flow rates may be used in an embodiment. The flow in line 12 from the body fluid source, such as the peritoneal cavity, to the electrofilter is 2000 ml/hour. Essentially all the fluid leaves the electrofilter in line 43. Some of the fluid also passes the nanomembrane of nanofilter, so that about 920 ml/hour passes to line 51, while about 1080 ml/hour passes via line 48 back to the electrofilter compartments 32 and 33. The fluid flow in line 76 will then be about 1080 ml/hour. The flow rate into the RO filter will be 920 ml/hour, and the excretion flow rate to vessel 60 will be 60 ml/hour. The flow rate in line 71 to the ultrafilter will be 860 ml/hour, which combine with 1080 ml/hour of line 76 to 1940 ml/hour. About 15 ml/hour is excreted from ultrafilter 70, mainly for transporting bacteria, virus and debris to the vessel 60, which leaves 1925 ml/hour in flow line 78 back to the patient. Thus, 75 ml/hour will be removed from the patient, which corresponds to 1800 ml/day.

If it is presumed that the creatinine concentration in the body fluid is about 0.5 mM (millimole/liter), the fluid in line 51 from the permeate outlet 46 of the nanofilter will comprise the same concentration. If a concentration ratio of 15:1 is obtained in the RO filter, the fluid in line 61 will comprise 7.5 mM, which will result in an excretion of 10.8 mmole per day. While some patients will have a production rate of creatinine in the area of 10-15 mmole per day, this excretion rate would be sufficient, while this type of patients producing much creatinine also would be able to tolerate 0.5-0.6 mM creatinine in the blood. If the urea concentration in blood is 40 mM, the excretion rate will be 864 mmole per day, which is above the production rate in a normal patient. If the patient produces more than 864 mmole per day, the urea concentration in blood would be larger, but this is normally no problem, since a patient can tolerate up to 100 mM urea in the blood without problems.

How much sodium and potassium that is excreted depends on the efficiency of the electrofilter 30. The body fluid in line 12 comprises about 140 mM sodium chloride. If 99% thereof is removed from the first compartment 31 to the third compartment 33, about 1.4 mM remains in the fluid passing via line 43 to the nanofilter and further to the RO filter. Thus, about 30 mmole sodium per day is excreted, which corresponds to 1.8 gram of salt. For potassium, the concentration in the body fluid is about 4 mM, resulting in about 0.04 mM in the line 43 and an excretion of about 0.864 mmole per day, i.e. about 0.07 gram. However, if only 90% is removed by the electrofilter, 10 times more salt is excreted, which is still acceptable and can be replaced by oral intake or salt in the food.

The embodiment shown may be altered in many respects. For example, the order of the nanofilter and the electrofilter may be reversed. Moreover, the ultrafilter is optional, or may be replaced by a sterile filter.

Figure 2:
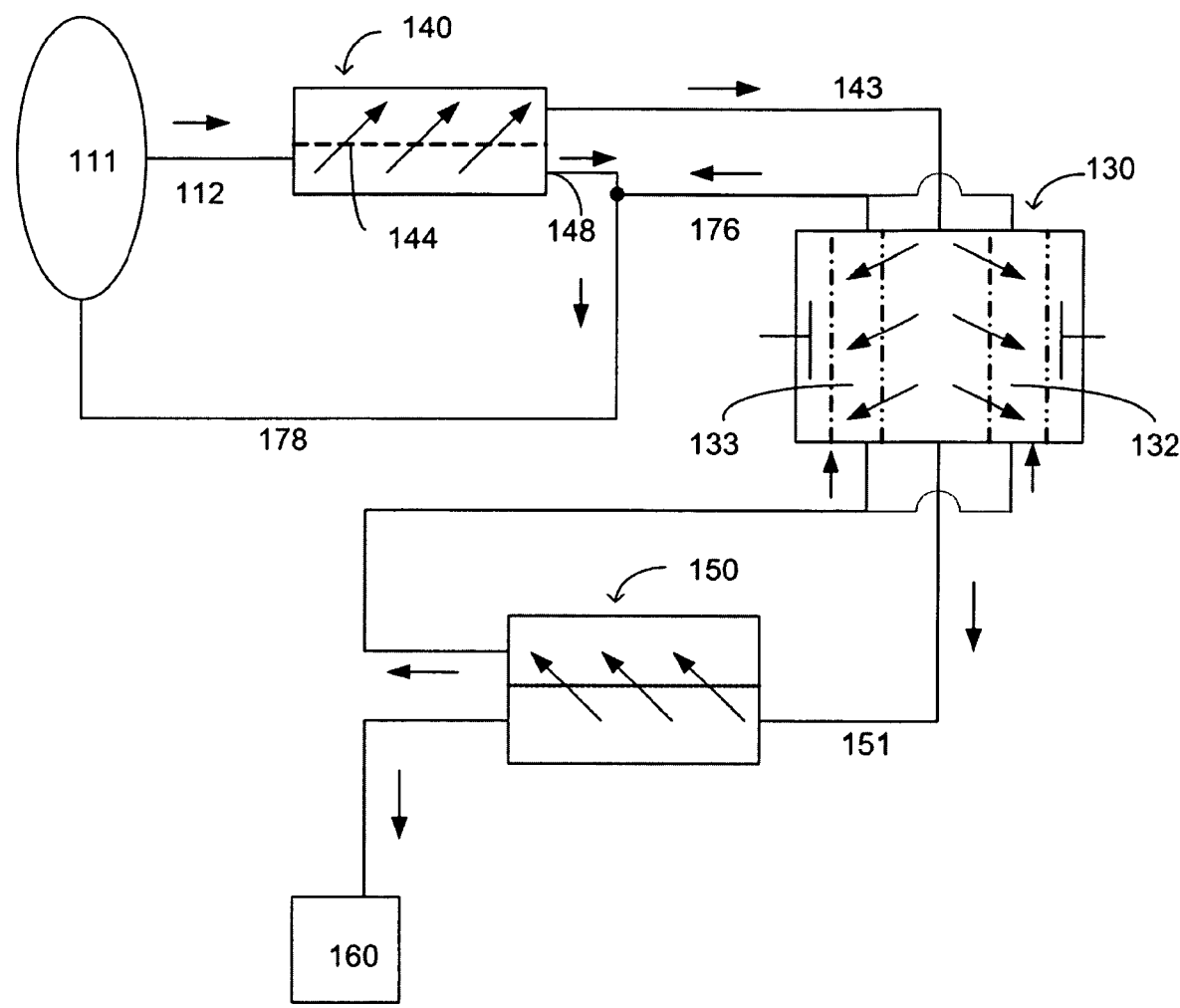
FIG. 2 is a schematic view of another embodiment.

Another embodiment is shown in FIG. 2. The same reference numerals have been used increased by 100. Thus, a body fluid is comprised in receptacle 111, which may be the peritoneal cavity of a patient. Fluid is taken out from the receptacle 111 at a rate of 2000 ml/hour and is circulated to a nanofilter 140 via line 112. A membrane 144 of the nanofilter has a cut-off of about 500 Da, passing urea, creatinine and smaller solutes and ions. Dextran 40, albumin, beta-2-microglobuline, bacteria, virus and debris are retained by the membrane 144 and returned to the receptacle 111 via line 148 at a rate of 500 ml/hour. The permeate fluid is passed to the electrofilter 130 via line 143 at a rate of 1500 ml/hour. Charged ions, such as sodium, potassium and chloride ions are separated by the electrofilter and the retentate fluid is passed via line 151 to the RO filter 150 at a rate of 1500 ml/hour. The retentate fluid is concentrated by the RO filter about 15 times and the water passing the RO membrane is returned to the outer compartments 132, 133 of the electrofilter in order to flush the ions passing through the ion exchange membranes. The fluid from the compartments 132 and 133 is returned to the receptacle 111 via line 176 at a rate of 1425 ml/hour.

It is presumed that the ion exchange membranes only pass charged ions, such as sodium, potassium and chloride ions, and do not pass uncharged substances or solutes, such as urea and creatinine, in spite of the fact that there is a large concentration gradient over the membranes of these substances.

The advantage of this embodiment is that substances like Dextran 40 and albumin will not pass through the electrofilter. Such substances may clog the filter and attach to the surfaces of the membranes of the electrofilter. However, virus and bacteria will circulate in the system. If desired, a sterile filter can be included in line 178 leading back to the receptacle.

Figure 3:
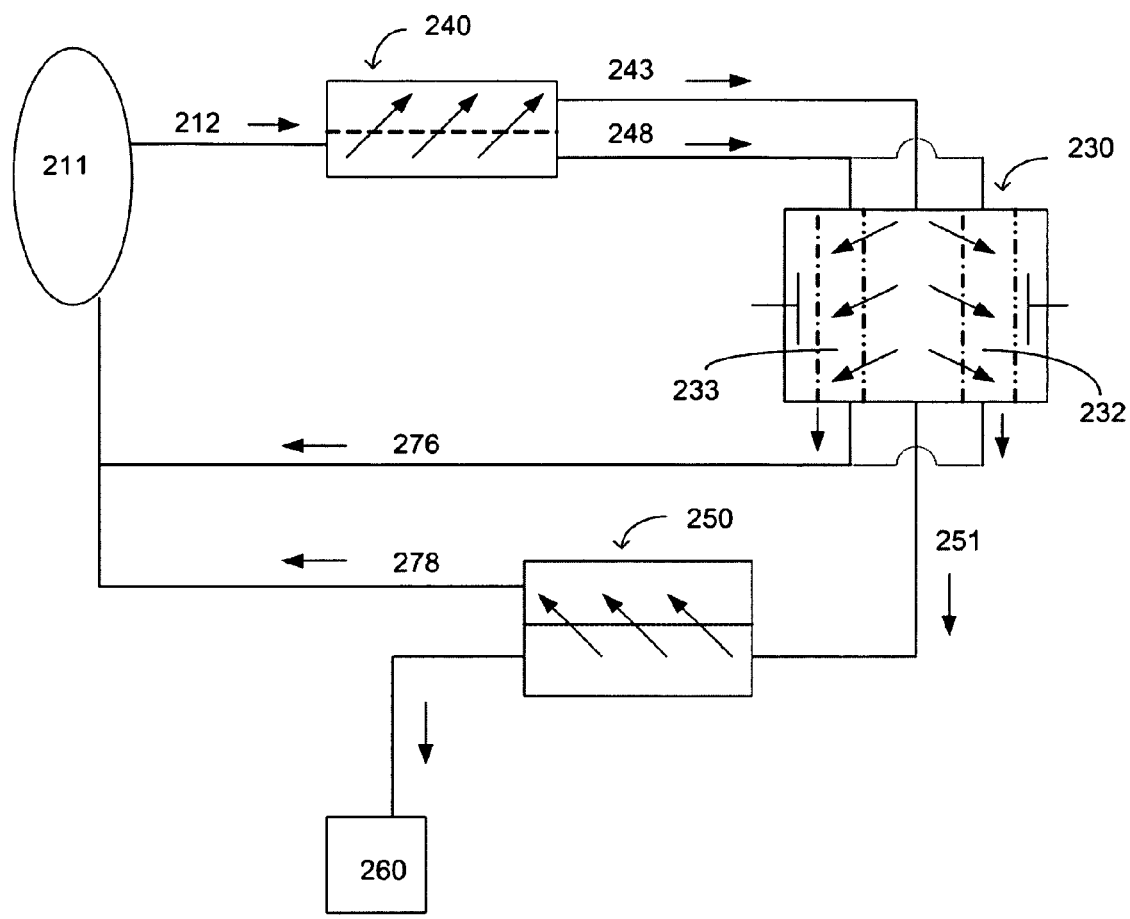
FIG. 3 is a schematic view of a further embodiment.

Another embodiment is shown in FIG. 3. It resembles the embodiment of FIG. 2, but the second and third compartment of the electrofilter are flushed by the retentate fluid of the nanofilter. The advantage of this design is that there is substantially no concentration gradient of urea and creatinine over the ion exchange membranes, so that these substances cannot pass these membranes.

The same reference numerals have been used increased by 200. The embodiment of FIG. 3 comprises a receptacle 211 comprising a body fluid. The body fluid is transferred to a nanofilter 240 by line 212 at a rate of 2000 ml/hour. The nanofilter membrane passes small solutes and ions, which are passed on to en electrofilter 230 via a line 243 at a rate of 1000 ml/hour. The retentate fluid of the nanofilter is passed to the second and third compartments 232 and 233 of the electrofilter to flush the separated ions, via a line 248 at a rate of 1000 ml/hour, which is then returned to the receptacle via line 276. The retentate of the electrofilter is passed via line 251 at a rate of 1000 ml/hour to the RO filter 250 for concentration. The retentate fluid of the RO filter forms the synthetic urine at a rate of 75 ml/hour into vessel 260. The water passing the RO membrane is returned to the receptacle 211 via line 278 at a rate of 925 ml/hour.

It may be difficult to remove 99% of the sodium in the electrofilter 30 in the embodiment shown in FIG. 1. In order to increase the removal, a second electrofilter may be used in the line 61 passing the retentate fluid of the RO filter 50 to the vessel 60. The concentration of sodium is relatively high in this line 61, which improves the separation.

Figure 4:
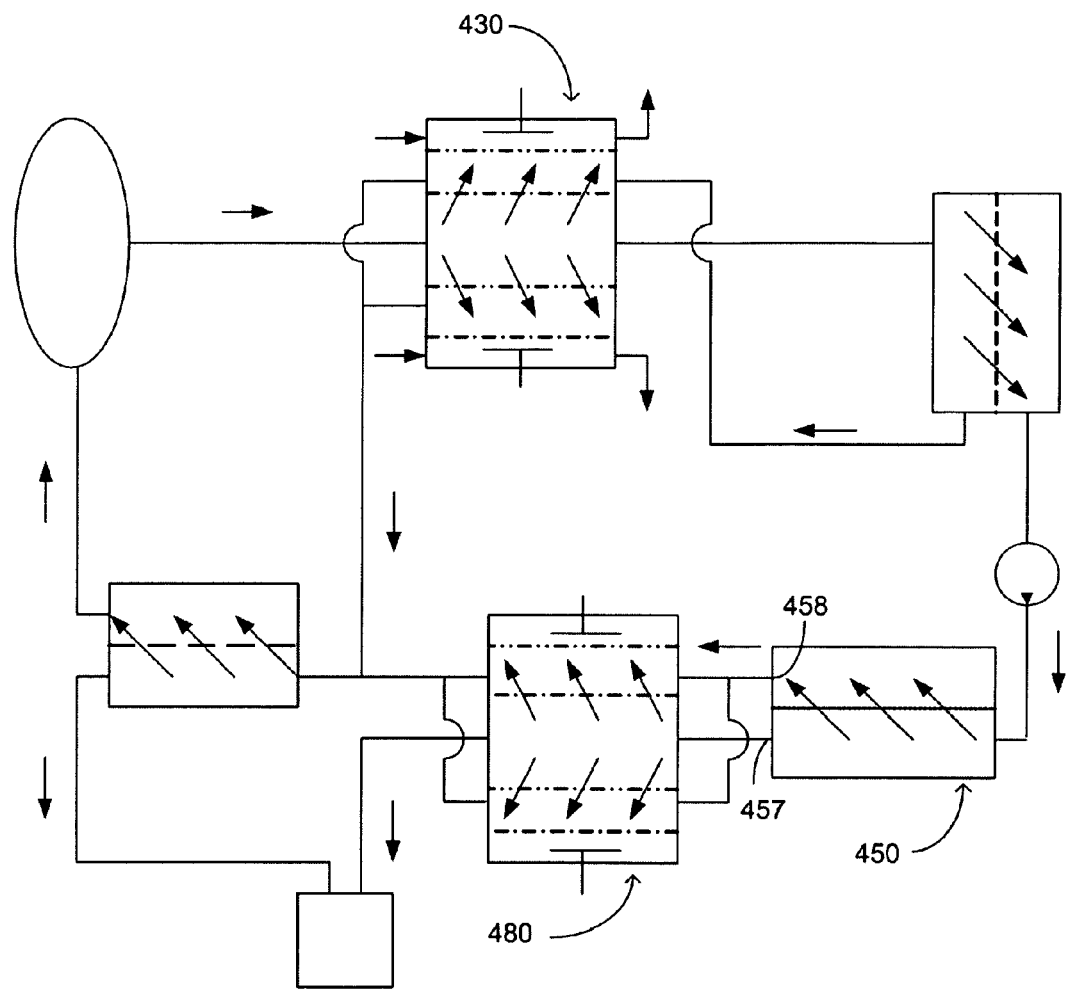
FIG. 4 is a schematic view of an embodiment, which is an alternative to the embodiment of FIG. 1.

An embodiment including this design is disclosed in FIG. 4. A second electrofilter 480 is included in the retentate outlet 457 from the RO filter 450. The clean water from the RO filter outlet 458 is used as flush fluid to remove the exchanged ions from the electrofilter as shown. In all other respects the embodiment of FIG. 4 is identical to the embodiment of FIG. 1. In an alternative embodiment, the first electrofilter 430 can be dispensed with. In a further alternative embodiment, the electrofilter 480 is flushed with fluid from the retentate outlet of the nanofilter.

Figure 5:
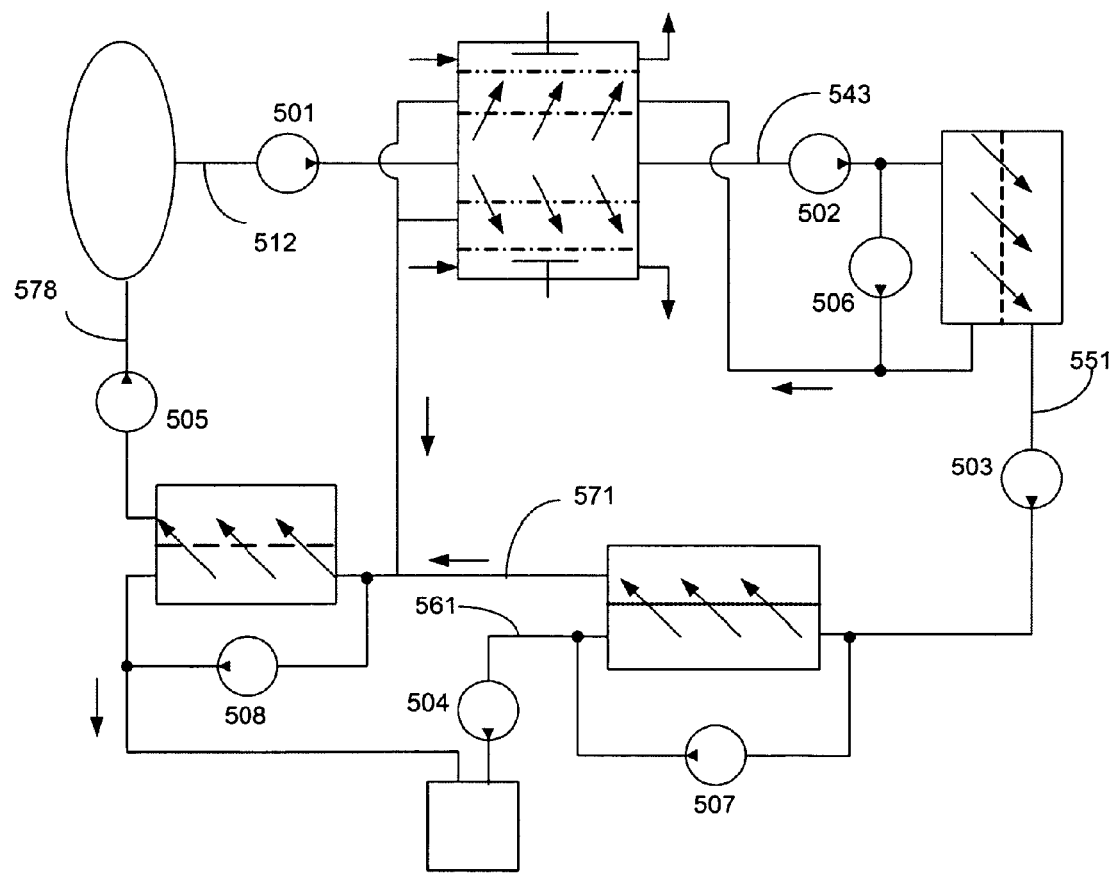
FIG. 5 is a schematic view of the embodiment of FIG. 1 including pumps.

FIG. 5 is a further detailed schematic diagram of the embodiment shown in FIG. 1 with pumps and restrictions added for controlling the flow rates. A first pump 501 is arranged in line 512 for controlling the flow rate to 2000 ml/hour. A second pump 502 is arranged in line 543 for controlling the flow rate to 2000 ml/hour. A third pump 503 is arranged in line 551 for controlling the flow rate to 920 ml/hour and for increasing the pressure for the operation of the RO membrane. A fourth pump 504 is arranged in the line 561 for controlling the excretion rate to 60 ml/hour. A fifth pump 505 is arranged in line 578 for controlling the flow rate to 1925 ml/hour, thereby removing 75 ml/hour from the patient.

Three pumps 506, 507 and 508 are arranged for increasing the flow along the membranes in order to improve the operation of the membranes. The flow directions may be the ones indicated on the drawing or the opposite.

The pressures will adjust themselves so that the flow rates are obtained. Only pump 503 needs to be designed in a special manner, for example as indicated in the international patent application PCT/SE2005/000212 mentioned above.

The pumps may be arranged in other manners than described above. Some pumps may be replaced by restrictions or valve, such as pump 504.

Figure 6:
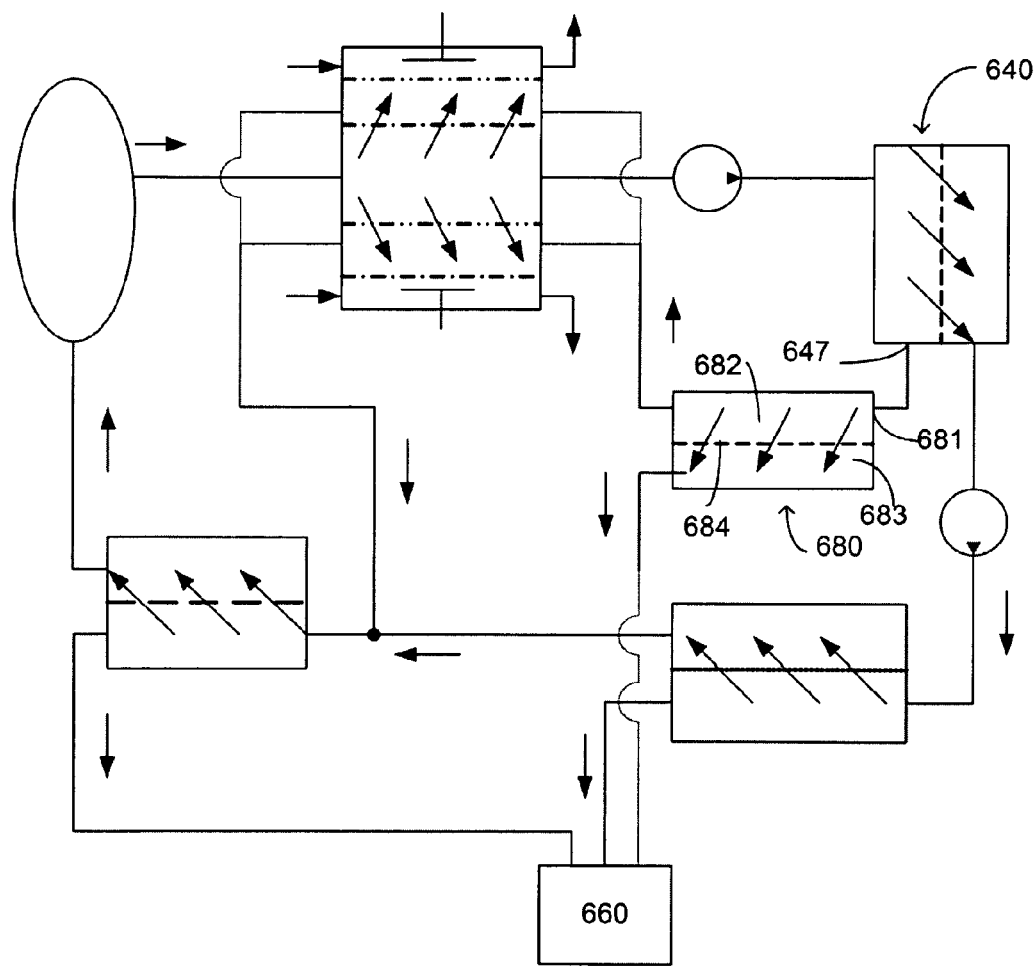
FIG. 6 is a schematic view of a still further embodiment.

It is sometimes considered essential to remove middle molecules like beta-2-microglobuline and similar solutes. The embodiment of FIG. 6 includes a middle molecule filter for removal of such substances. The embodiment shown in FIG. 6 is based on the embodiment of FIG. 1. The retentate fluid of the nanofilter 640 is depleted on charged ions, since it has passed the electrofilter, and is enhanced of large molecules, which cannot pass the membrane of the nanofilter. This retentate fluid is passed from the retentate outlet 647 of the nanofilter and to the inlet 681 of a middle molecule filter 680 having a first compartment 682 and a second compartment 683 separated by a membrane 684. The membrane may have a cut-off of about 15000 Da, thereby passing solutes smaller than 15000 Da. Such solutes are for example beta-2-microglobuline and other similar substances. The retentate fluid in the first compartment is passed as flushing fluid to the electrofilter as in the embodiment of FIG. 1, while the permeate fluid is given off, for example to the vessel 660, possibly after concentration. In this way, middle molecules can be excreted. At the same time other small solutes also present in the retentate fluid from the nanofilter are excreted. Albumin and other large molecules are retained.

The above embodiments have been described using a peritoneal dialysis fluid as a body fluid. The peritoneal fluid comprises Dextran 40 as a means for extracting water from the blood over the peritoneal membrane by osmosis. Thus, Dextran 40 should be retained in the system and not excreted in the synthetic urine. Dextran 40 is a polysaccharide having a molecule size of about 40000 Da. However, the molecule is relatively long and narrow and may relatively easily pass a membrane of an ultrafilter having a cut-off around 50000 Da.

The peritoneal fluid is installed in the patient in a conventional way before the system according to the present embodiment is put into operation. There may be around 2 liters in total, of which about 1 liter is present in the body and one liter is present in the extracorporeal circuit for regeneration. The flows out of and into the peritoneal cavity should be monitored so that no pressure gradient is generated, which may be inconvenient to the patient. The ultrafiltration, i.e. the volume gain due to the osmosis action of Dextran 40, occurs automatically in dependence of concentration gradients, and the flow rates should be adapted thereto. Thus, the flow rates given above are only to be seen as examples, and can be altered or adjusted in many respects.

The body fluid may be plasma obtained from a plasma filter. A plasma filter may be extracorporeally arranged and blood is taken out from the body and returned to the body after passing the plasma filter. The plasma filter may be an ultrafilter having a membrane with a cut-off of from about 500 Da to about 50000 Da, such as 500 Da or 50000 Da. The permeate forms the plasma. The plasma is regenerated according to the present invention. The regenerated plasma may be returned directly to the blood before of after the plasma filter, or even directly to the circulatory system of the patient via a catheter.

Alternatively, the regenerated plasma is returned to the plasma filter, which then operates like a dialysis filter. The regenerated fluid becomes the dialysis fluid, passing on one side of a semi-permeable membrane while blood passes on the other side of the membrane. Such a dialysis fluid is included within the expression "body fluid" in the present context.

Figure 7:
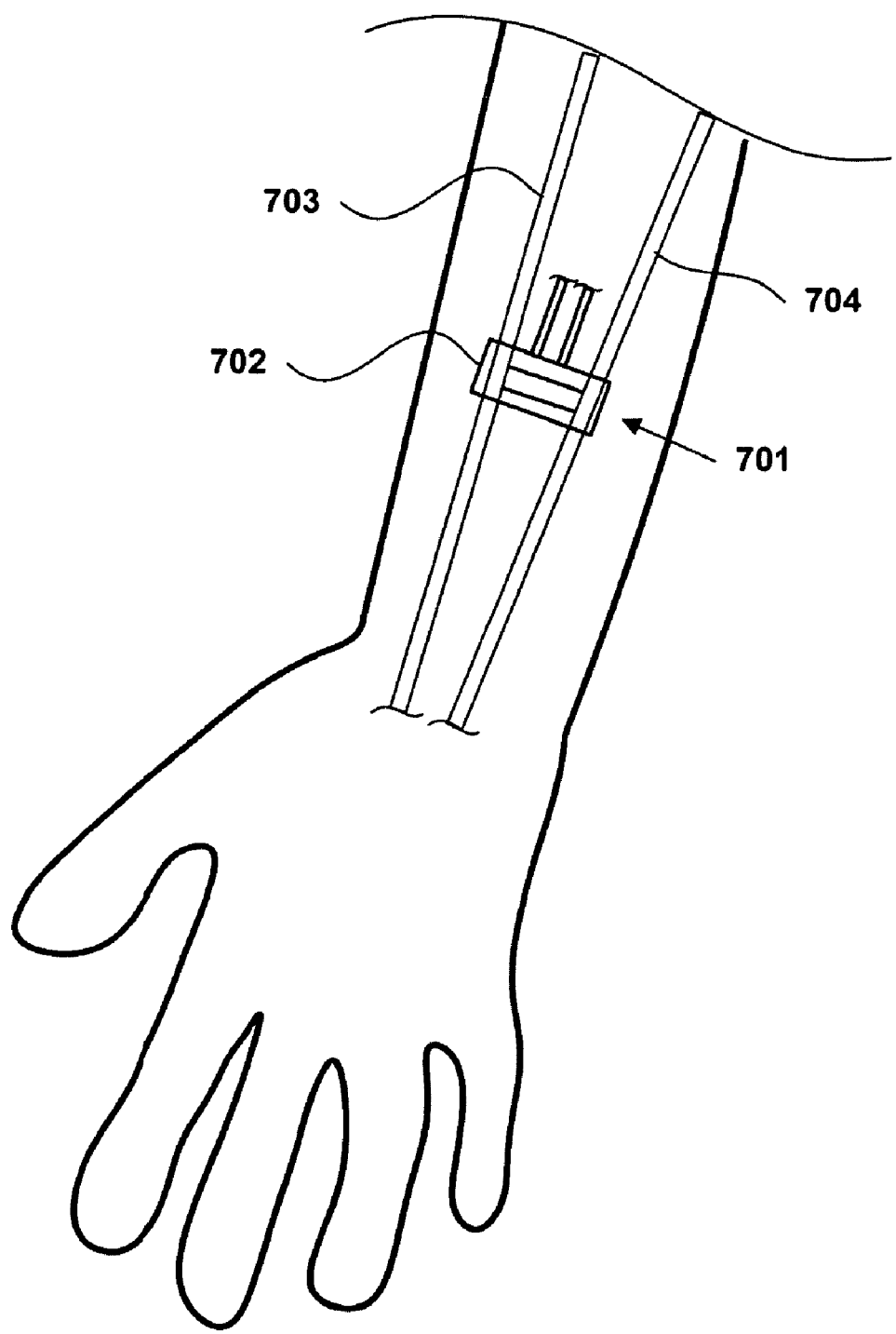
FIG. 7 is a schematic view of an arm of a patient with an endogenous filter.
Figure 8:
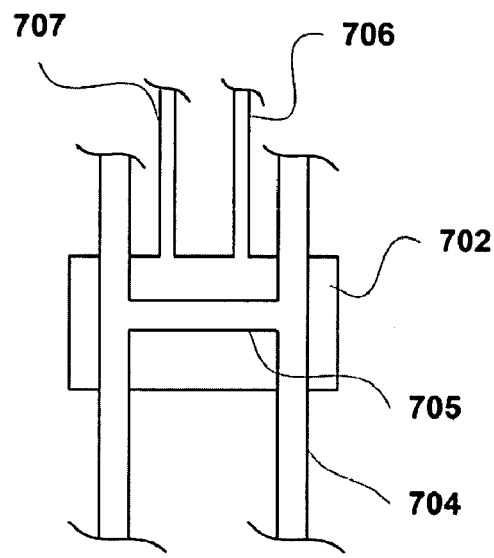
FIG. 8 is a schematic view of the endogenous filter of FIG. 7 is more details.

The filter may be endogenous, as shown in FIG. 7. The endogenous filter 701 comprises a housing 702, which is arranged to be surgically inserted in for example an arm of a patient. The housing encloses an artery 703 at one end and a vein 704 at the other end. A tube 705 is surgically arranged between the artery and the vein inside the housing 702, similar to an artery-venous fistula. The tube 705 is made from a semi-permeable material passing small solutes, and may have a cut-off of about 500 Da or 50000 Da. The housing is provided with an inlet 706 and an outlet 707. A fluid is circulated from the inlet 706 to the outlet 707 around the tube 705 to perform exchange of substances through the tube membrane by diffusion and/or convection. The fluid is taken out from the body via outlet 707 as said body fluid and regenerated by the system of any of the embodiments described. Then, the regenerated fluid is returned to the inlet 706. A pump may be arranged to provide the fluid flow and to provide a negative pressure inside housing 702 to promote removal of water from the blood. Thus, the endogenous filter operates as a dialysator.

Figure 9:
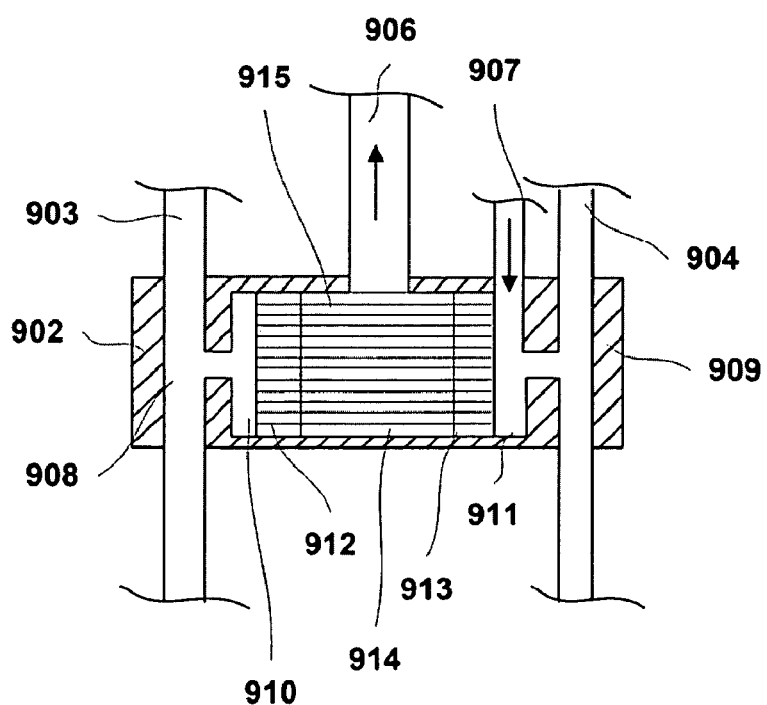
FIG. 9 is a schematic view of another endogenous filter design.

In order to increase the surface area of the membrane, the tube may be replaced by a bundle of hollow fibers as shown in FIG. 9. The hollow fibers may be straight as shown in FIG. 9, or may be arranged in circles or other paths.

FIG. 9 discloses a housing 902 comprising two openings 908 and 909 for enclosing a part of an artery 903 and a vein 904, respectively. The artery is connected to a first compartment 910 of the housing and the vein is connected to a second compartment 911 of the housing as shown. The compartments are limited by a plug 912 and 913, respectively, and several hollow fibers 915 extend between the plugs 912 and 913. A plasma compartment 914 is formed between the plugs 912 and 913 and is connected to the outlet 906. Blood is flowing from the artery to the artery compartment 910 and through the interior of the hollow fibers 915 to the vein compartment 911 and further to the vein 904. Plasma is passing through the walls of the hollow fibers 915 into plasma compartment 914 and out to the extracorporeal circuit via outlet 906, in any conventional way. The regenerated fluid from the system of the embodiment may be passed to the vein compartment 911 via inlet 907, i.e. post-infusion. Alternatively, pre-infusion may be used by returning the regenerated fluid to the artery compartment 910 (not shown).

The inlets 706, 907 and outlets 707, 906 may be tubes ending with a rubber membrane positioned just below the skin of the patient. Needles may penetrate the skin and the rubber membrane to get access to the outlet and inlet, respectively.

The regeneration according to the embodiments does not add water or compositions to the body fluid, but only removes and excrete water and products or substances, i.e. forms synthetic urine.

In patients having impaired or no kidney function, the blood will normally become acidic. In dialysis, this is counteracted by adding bicarbonate to the dialysis fluid. In the present embodiments, the patient may take in bicarbonate orally or in any other suitable way. Other methods may be used as well.

In the above embodiments, certain substances, ions or molecules have been indicated. However, it is appreciated, that further substances are present in the body fluid, such as endotoxins, that have a molecule size of from some hundred Dalton and upwards, and are excreted if they can pass the nanofilter.

The exclusion limit or cut-off of each filter is indicated in the description of the embodiments. However, such exclusion limits can be different than those described.

The nanofilter may be designed to retain the osmotic active agent in a peritoneal fluid, such as Dextran 40, which is a molecule having a size of 40000 Da. If the nanofilter has an exclusion limit of between about 200 Da to 1000 Da, only small molecules will pass the filter and be excreted. If the nanofilter has an exclusion limit of between about 1000 Da to about 15000 Da, also middle size molecules will be excreted. If the nanofilter has an exclusion limit between about 15000 Da to about 40000 Da, there is a risk that Dextran 40 will permeate through the membrane and be excreted to the synthetic urine, which is non-desired. Dextran 40 is a long molecule that may pass smaller pores than 40000 Da.

In the case of dialysis fluid and plasma as the body fluid to be regenerated, the nanofilter may have an exclusion limit of up to 50000 Da in order to retain albumin and other large molecules.

The electrofilter should have a low exclusion limit of below about 100 Da, such as below 50 Da, in order to pass only the small ions, and retain molecules like urea and creatinine.

The ultrafilter should have an exclusion limit of about 50000 Da in order to pass Dextran 40 but exclude i.a. beta-2-microglobuline. The ultrafilter can be exchanged with a sterile filter having an exclusion limit of below about 1000000 Da, or below about 200000 Da.

The sizes of the different filters are designed so that a sufficient flow is obtainable. The filters may be small, such as below about 0.5 m$^2$, such as below about 0.2 m$^2$.

Hereinabove, several embodiments of the invention have been described with reference to the drawings. Such embodiments include different separate features combined in a specific manner in each embodiment. However, the features may be combined in other manners than those explicitly described. The invention is not limited by the described embodiments but only by the appended patent claims.

The invention claimed is:

1. A system for regeneration of a body fluid, comprising:
a line for removing a body fluid from a patient;
a filter unit for retaining at least one component of the body fluid as a retentate fluid and for passing other components as a permeate fluid;
a reverse osmosis filter for concentrating the permeate fluid of the filter unit, for producing a synthetic urine to be discarded as a retentate fluid and essentially water as a permeate fluid;
a return line for returning the permeate fluid of the reverse osmosis filter and the retentate fluid of the filter unit to the body of the patient; and
an electrofilter for removing charged ions from the body fluid and returning said ions to the patient.

2. The system according to claim 1, wherein said electrofilter is arranged before said reverse osmosis filter.

3. The system according to claim 2, wherein a second electrofilter is arranged after said reverse osmosis filter for removing charged ions from the synthetic urine.

4. The system according to claim 1, wherein the electrofilter comprises an anode and a cathode and ion exchange membranes, whereby a source of electric power is to be applied over the anode and cathode.

5. The system according to claim 4, wherein a first compartment is formed in the electrofilter between a cation membrane and an anion membrane, in which said body fluid is entered, and a second compartment is formed at the other side of the cation membrane and a third compartment is formed at the other side of the anion membrane, wherein a flushing fluid is arranged to pass through said second and said third compartments to flush out the ions separated by the membranes.

6. The system according to claim 5, wherein said flushing fluid is the retentate fluid of the filter unit or the permeate fluid of the reverse osmosis filter.

7. The system according to claim 1, further comprising an ultrafilter arranged in the return line to the patient.

8. The system according to claim 1, wherein the filter unit is a nanofilter having a membrane with a cut-off of about 500 Da.

* * * * *